US006299131B1

(12) United States Patent
Ryan (10) Patent No.: US 6,299,131 B1
(45) Date of Patent: Oct. 9, 2001

(54) SWABBABLE NEEDLELESS INJECTION PORT SYSTEM HAVING LOW REFLUX

(75) Inventor: Dana Wm. Ryan, Woodward, OK (US)

(73) Assignee: Rymed Technologies, Inc., Woodward, OK (US)

( * ) Notice: Subject to any disclaimer, the term of this patent is extended or adjusted under 35 U.S.C. 154(b) by 0 days.

(21) Appl. No.: 09/568,478

(22) Filed: May 9, 2000

Related U.S. Application Data

(62) Division of application No. 09/166,559, filed on Oct. 5, 1998, now Pat. No. 6,113,068.

(51) Int. Cl.[7] ................................................ A61M 39/26
(52) U.S. Cl. ........................................ 251/149.1; 604/905
(58) Field of Search .......................... 251/149.1, 149.4, 251/149.6; 604/256, 905, 249, 167.03, 246; 206/206, 207

(56) References Cited

U.S. PATENT DOCUMENTS

| 2,783,908 | * | 3/1957 | Winfield ................................. 215/247 |
| 4,440,207 | | 4/1984 | Genatempo et al. ................. 150/52 R |
| 4,610,469 | | 9/1986 | Wolff-Mooij .......................... 285/260 |
| 4,863,453 | * | 9/1989 | Berger et al. ..................... 604/415 X |
| 5,065,783 | | 11/1991 | Ogle, II ................................. 137/68.1 |
| 5,122,123 | | 6/1992 | Vaillancourt .......................... 604/192 |
| 5,147,329 | | 9/1992 | Brannon ................................. 604/231 |
| 5,242,432 | | 9/1993 | DeFrank ................................. 604/284 |
| 5,251,873 | | 10/1993 | Atkinson et al. ................... 251/149.1 |
| 5,269,771 | | 12/1993 | Thomas et al. ....................... 604/213 |
| 5,360,413 | | 11/1994 | Leason et al. ........................ 604/249 |
| 5,395,348 | | 3/1995 | Ryan ..................................... 604/247 |
| 5,439,451 | | 8/1995 | Collinson et al. .................... 604/247 |
| 5,487,728 | | 1/1996 | Vaillancourt .............................. 604/86 |
| 5,492,147 | | 2/1996 | Challender et al. ............. 137/614.05 |
| 5,514,116 | | 5/1996 | Vaillancourt .......................... 604/283 |
| 5,518,005 | | 5/1996 | Brannon ................................. 128/765 |
| 5,520,666 | | 5/1996 | Choudhury et al. .................. 604/283 |
| 5,535,771 | | 7/1996 | Purdy et al. ............................. 137/15 |
| 5,536,258 | | 7/1996 | Folden ................................... 604/265 |
| 5,549,566 | | 8/1996 | Elias ...................................... 604/167 |
| 5,549,577 | | 8/1996 | Siegel et al. .......................... 604/256 |
| 5,611,792 | * | 3/1997 | Gustafsson ....................... 604/905 X |
| 5,618,268 | | 4/1997 | Raines et al. ........................... 604/82 |
| 5,645,538 | | 7/1997 | Richmond ............................. 604/256 |
| 5,658,260 | | 8/1997 | Desecki et al. ....................... 604/239 |
| 5,669,891 | | 9/1997 | Vaillancourt .......................... 604/283 |
| 5,694,686 | | 12/1997 | Lopez ..................................... 29/890 |
| 5,741,121 | | 4/1998 | O'Leary ................................. 417/53 |

(List continued on next page.)

Primary Examiner—Kevin Shaver
Assistant Examiner—Eric Keasel
(74) Attorney, Agent, or Firm—David P. Gordon; David S Jacobson; Thomas A Gallagher (57) ABSTRACT

A needleless IV injection port assembly includes a spiked body provided with a hollow spike, a female luer component, a flexible and resilient spike boot having a tip and spring portion, a centering member, and a resilient swabbable septum. The spike boot extends over the spike, the centering member is provided over a portion of the spike and spike boot, and the septum is provided between the centering member and an end of the female luer component. The spiked body and the female luer component are secured together to complete the assembly. The length of the female luer component and/or the length of the spike is chosen so that when a separate male luer is positioned over a protuberance on the septum and pushed into the female luer component, the male luer places pressure upon the septum which thereby urges the septum toward the spike. The pressure on the septum causes the spring portion of the boot to be compressed and the tip portion of the boot to be pierced by the tip of the spike. As the septum is further compressed, the septum extends over the spike, with a pre-slit hole in the septum facilitating the extension thereover, such that a hollow of the spike is in fluid communication with the male luer connector. The injection port causes minimal reflux, and the spike boot and septum provide a swabbable antibacterial double barrier over the spike.

13 Claims, 8 Drawing Sheets

U.S. PATENT DOCUMENTS

| | | | |
|---|---|---|---|
| 5,788,215 | 8/1998 | Ryan | 251/149.6 |
| 5,806,831 | 9/1998 | Paradis | 251/149.1 |
| 5,839,715 | 11/1998 | Leinsing | 251/149.1 |
| 6,022,339 * | 2/2000 | Fowles et al. | 604/411 |

* cited by examiner

SWABBABLE NEEDLELESS INJECTION PORT SYSTEM HAVING LOW REFLUX

This application is a division of Ser. No. 09/166,559 filed Oct. 5, 1998 now U.S. Pat. No. 6,113,068.

BACKGROUND OF THE INVENTION

1. Field of the Invention

This invention relates to medical IV administration line connectors. More particularly, this invention relates to needleless injection ports for the safe infusion and/or aspiration of fluids in intravenous and blood administration therapy.

2. State of the Art

Intravenous therapy has a long history of use in supplying patients with pharmaceuticals, liquid nourishment, or blood products. Prior art FIGS. 1 through 4 show that the current or conventional way of introducing parenteral liquid solutions and/or blood and blood products into a patient is by the conventional gravity feeding system 10. The feeding system 10 includes a container 12 that is either a bottle or bag for the parenteral solution, a tube 14 extending from the bottle or bag and connected to a Y-injection site 16 (piggyback or secondary Y-injection site), and a tube 18 from the Y-injection site 16 to a needle or catheter 20 which is inserted into a vein in the arm 22 of the patient. The vein-access needle or catheter is taped to the patient with adhesive tape 24 so that the chance of a detachment and disconnect from the vein is minimized.

Supplemental intravenous therapy from a piggyback or secondary bottle or bag 26 is introduced through the Y-injection site 16 into the primary intravenous administration set 10. As seen best in FIG. 3, the Y-injection site 16 which is integrated into the primary intravenous administration set 10 consists of two tubular conduits 16a, 16b which merge into a third tubular conduit 16c. The tubing 12 from the bottle or bag of parenteral solution of the primary intravenous administration set 10 is attached into the inlet port 16a of the Y-injection site. In similar fashion, the tube 18 is attached into the exit port 16c of the Y-injection site. A sealed entry port segment 17 of the Y-injection site 16 is provided by the extension conduit 16b which has a standard self-sealing latex rubber septum 17a at its inlet port to seal this port from leakage. Consequently, it is difficult for pathogens to enter the Y-injection site 16 via the septum port 17 because of the seal 17a. This self-sealing septum 17a is of a conventional design and includes coaxial annular aprons which fit over the conduit wall and grip the external and internal wall surfaces to hold the septum securely to the conduit 16b. Typically, a plastic shrink-band (not shown) is shrunk on the outer wall of the septum 17a to securely connect it to the extension conduit 16b.

Figure 3:
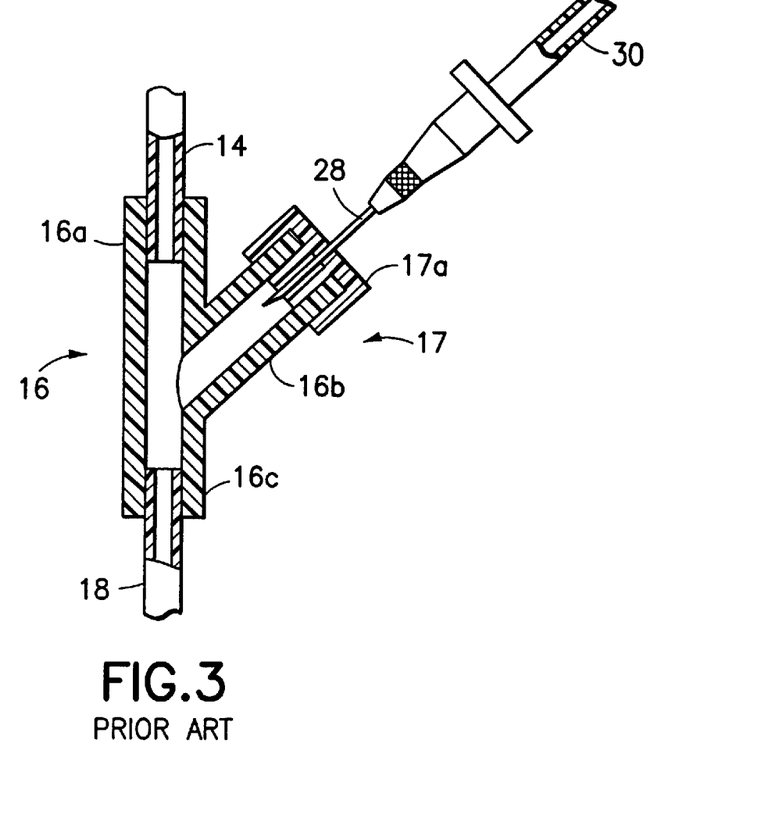
FIG. 3 is a broken side elevation view, in partial section, of a prior art Y-injection site.

The supplemental intravenous solution is introduced into the primary intravenous administration set 10 through the Y-injection site 16 by way of a primed piggyback or secondary intravenous set 26. The piggyback or secondary intravenous set 26 has a hollow-bore needle 28 attached to its distal end, which in turn is inserted through the self-sealing septum 17a of the Y-injection site 16 and into the extension conduit 16b. This needle 28 is connected to a tube 30 which is connected to a drip-chamber (not shown) of the piggyback or secondary intravenous set 26. A roller clamp 14a, 30a is typically used on both the primary and piggyback/secondary intravenous sets to control liquid flow rates into the patient.

There are several problems associated with the standard techniques employed for intravenous therapy. If the piggyback needle 28 is not securely taped to the Y-injection site 16 and the primary intravenous administration set tubing 12, 18, patients can move their arms, or roll over in bed accidentally pulling the needle 28 completely out of the septum 17a on the Y-injection site 16. If this occurs, the self-sealing latex septum 17a will close off automatically and not allow liquid or contamination to enter the primary intravenous administration set 10. The primary intravenous solution in the bottle or bag 12 will continue to flow into the patient, but, the necessary supplemental pharmaceutical solution from the piggyback or secondary bottle or bag 26 will no longer flow into the patient via the Y-injection site 16. The consequences to the patient for this situation can lead to serious complications and even death if the condition is not noticed by a clinician immediately. Even if the clinician notices the detachment of the needle 28 from the Y-injection site septum 17a immediately, the needle 28 is now contaminated with pathogens and should never be introduced back into the septum 17a. A new sterile, piggyback/secondary intravenous set must be opened, primed, and a new hollow-bore needle reinserted back into the septum on the Y-injection site. Additionally, whether the needle 28 is accidentally detached, or, the clinician removes the needle 28 from the Y-injection site septum once the supplemental pharmaceutical therapy is completed for the patient, the exposed needle 28 is contaminated with pathogens and must be safely disposed by the clinicians without accidentally sticking themselves.

To avoid accidental removal, the needle of the piggyback or secondary intravenous set may be taped to the Y-injection site and extension port. When this occurs, the needle may be secured from detachment, but the needle cannot be easily and safely removed by the clinician when the supplemental pharmaceutical therapy is completed, thereby creating a higher incidence for an accidental needle stick injury. Also, because clinicians hold the Y-injection site with one hand while the other hand is used to insert the needle into the Y-injection site septum, the clinicians may accidentally stick the needle directly into their hands holding the Y-injection site, or stick the needle completely through the Y-injection site wall into their hands.

Figure 1:
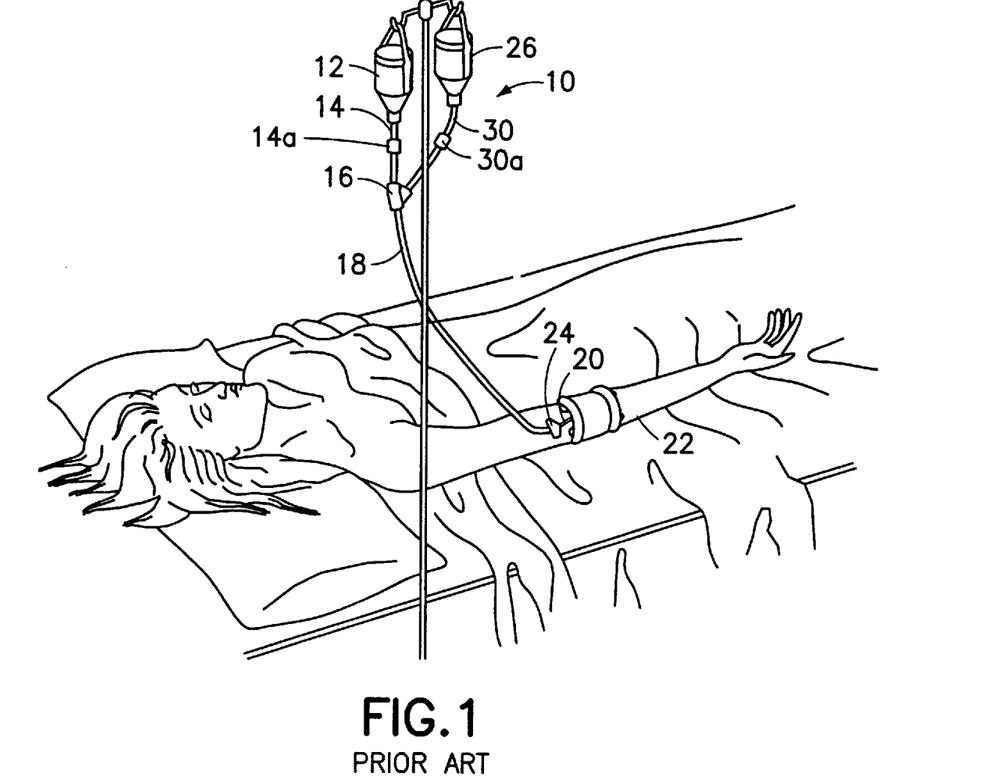
FIG. 1 is a schematic view of a prior art intravenous administration set coupled to a patient.
Figure 2:
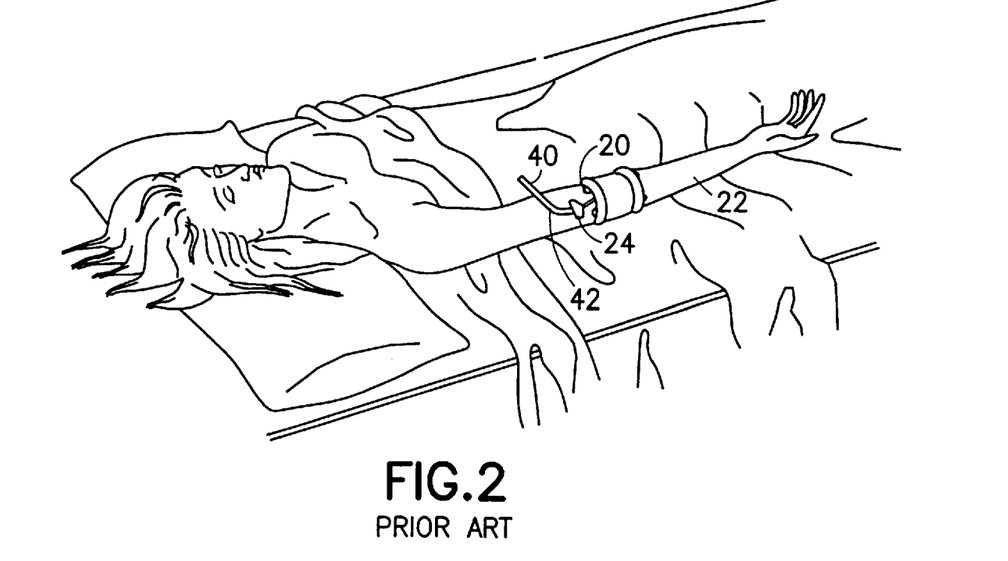
FIG. 2 is a view similar to FIG. 1 of a prior art "intermittent" intravenous administration set coupled to a patient.
Figure 4:
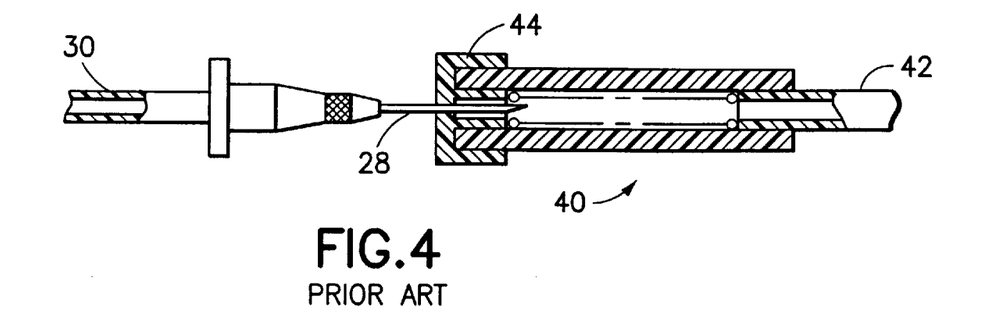
FIG. 4 is a broken side elevation view, in partial section, of a prior art heparin lock injection port.

The above description and problems associated with conventional continuous and supplemental intravenous therapy through a Y-injection site is similar to the problems associated with intermittent intravenous therapy using a "Heparin Lock" injection port 40 (FIGS. 2 and 4). A heparin lock injection port 40 is either connected directly to the vein-access device 20, or attached to a short catheter extension tubing set 42 typically with microbore tubing which is attached to the vein-access device as shown in FIG. 2. The heparin lock has a self-sealing septum port 44 which is similar to the septum port 17 described above. A conventional intermittent intravenous therapy could utilize a short-term primary intravenous administration set 26 with a hollow-bore needle 28 attached to the distal end of a tube 30. The needle would be inserted to the self-sealing septum found on standard heparin lock injection port 40. Another means of introducing supplemental intermittent pharmaceuticals to a patient is to perform an intravenous push utilizing a syringe with a hollow-bore needle attached. The drug is pushed into the patient through the heparin lock injection port 40. Once dispensed, the syringe/contaminated needle is removed from the self-sealing septum 44 on the heparin lock injection port 40.

As set out above, the common medical techniques for delivering supplemental liquid fluids to the patient necessitates the use of a hollow-bore needle. The needle is either attached to a secondary intravenous set or a syringe, and is inserted through the self-sealing rubber stopper on the heparin lock injection port or the Y-injection port that is integrated into the primary intravenous administration set. Typically, the needle is secured to the injection port only with tape. The needle can detach from the injection port resulting in a serious or fatal interruption of the flow of the intravenous solutions to the patient. Moreover, the exposed needle can easily be contaminated by contact with non-sterile objects. Sound aseptic techniques must be practiced by the healthcare professional in order to ensure that the sterile needle does not become contaminated and cause a nosocomial infection to the patient.

Since the discovery of the HIV virus that causes AIDS in the mid-1980's, a major concern among healthcare workers practicing the standard methods of delivering intravenous therapy is accidental needle sticks with a contaminated needle. When a needle is removed from an injection port, it may be contaminated with the patient's blood. The contaminated needle must be carefully disposed in a sharps container. While handling the needle during removal and disposal, clinicians may, and often do, inadvertently stick themselves. Among all of the needled medical devices used in healthcare facilities, contaminated intravenous needles are responsible for the most accidental needlestick injuries. When a needlestick injury occurs, the clinician must stop work and have a blood test performed. Since a needlestick injury can result in fatal disease, the injured clinician will also experience tremendous emotional trauma.

There is a wealth of prior art concerned with the problem of accidental needlesticks. Needleless valves are known in the art of intravenous administration. For example, see my prior U.S. Pat. No. 5,395,348. In particular, with respect to "heparin lock"-type connectors, several design criteria have been determined for the satisfactory functioning of the connector. First, a fluid flow of at least 150 mL per minute at gravity is desirable. Second, it is desirable to limit the priming volume to not more than 0.05 mL. Third, it is desirable to provide with valve connector with as little dead space as possible. The amount of dead space is of great concern, especially when designing an injection port which will be coupled to an intravenous line. When a valve is closed, i.e., after the injection of a drug and removal of the syringe, the dead space can cause reflux; that is, a backflow of fluid into the valve which can draw an amount of blood equal to the volume of the dead space into the intravenous line. The blood can coagulate and obstruct the flow through the intravenous line, at least necessitating the use of a new intravenous line, and possibly causing severe detrimental effect to the patient. My U.S. Pat. No. 5,788,215, provides an injection port system which meets these requirements. The unit is non-swabbable; i.e., it has no exposed surface at the location of receiving an injection of a fluid into the valve and, as such, has good antiseptic properties.

However, health care professionals, through habit, prefer a system which is swabbable; that is, which has an exposed surface which can be cleansed (for example, with an alcohol-soaked cotton swab) prior to injection of a drug or parenteral solution therethrough. A consequence of providing an exposed swabbable surface is the increased susceptibility of bacterial buildup at or surrounding the surface barrier. It is difficult to contain the bacteria from penetrating the barrier.

Several prior art swabbable needleless injection port systems are known, but each has one or more disadvantages. For example, the Posiflow™ by CDC NIMA has a substantially low fluid flow rate (approximately 60 mL per minute) and significant fluid reflux (0.02 mL). In addition, while the unit is swabbable, the barrier is not satisfactorily microbial resistant. The UltraSite™ by Braun has a relatively large priming volume (0.35 mL). The SmartSite™ by Alaris has a relatively low fluid flow rate (approximately 120 mL) and a very large reflux (0.05 mL). The InterLink™ by Baxter has a very large priming volume (0.24 mL) and a large fluid reflux (0.04 mL). The ICU CLC2000™ has low reflux of fluid, but uses a piston-type valve which causes fluid to be forced out of the injection port around the luer connector. The difficulty in designing a needleless injection port connector which achieves all of the mechanical and antibacterial requirements is evidenced by the fact that several previously commercially available injection port systems have been recently removed from the market for unsatisfactory performance.

SUMMARY OF THE INVENTION

It is therefore an object of the invention to provide a needleless medical injection port which is safe, efficacious, and easy to use.

It is also an object of the invention to provide an injection port valve system which is swabbable and provides an excellent antibacterial barrier.

It is another object of the invention to provide an injection port valve system which has minimal fluid reflux.

It is an additional object of the invention to provide an injection port valve system which has a small priming volume.

It is yet another object of the invention to provide an injection port valve system which centers a male luer connector being coupled thereto.

In accordance with the objects stated above, a swabbable needleless IV injection port assembly is provided for coupling to and uncoupling from a first fluid pathway (e.g., an IV line having a first connector) and for receiving and passing a fluid into the first fluid pathway from a device (e.g., a syringe provided with a second connector) into the first fluid pathway. The injection port assembly generally comprises a body provided with a hollow spike (hereinafter a "spiked body"), a female luer connector component (preferably a luer lock), a flexible and resilient spike boot, a centering member, and a resilient septum. The spiked body includes a male luer connector at a first end and a preferably integrally formed spike having a tip at a second end. The juncture of the male luer connector and the spike form a base, and the spike and male luer connector define a fluid pathway which extends completely therethrough. The base includes an annular groove about the spike and a first mating means. The female luer connector component includes a first open end provided with a flange, a second end having a preferably tapered opening and preferably a luer lock configuration, and a central portion which extends over the spike. The flange includes a second mating means which is coupled to the first mating means on the base of the spiked body. The spike boot includes a tip portion which covers the tip of the spike, a radially enlarged portion adjacent the tip portion, a preferably spring-like portion extending along a shaft of the spike, and a base portion which seats in an annular groove in the base of the body. The centering member includes a generally tubular outer portion and an annular central portion defining a hole and having first and second sides.

In assembly, the boot is positioned over the spike with the base of the boot seating in the annular groove in the base of the spiked body. The centering member is positioned over the tip of the spike and tip portion of the spike boot, the septum is provided over the centering member, and the female luer connector component is extended over the septum, centering member, spike and boot. The tip of the spike and tip portion of the boot extend through the hole in the annular portion of the centering member, and the first side of the annular portion abuts the radially enlarged portion of the boot to center the boot within the female luer connector. The septum seats between the second end of the female luer connector and the second side of the annular portion of the centering member (at a peripheral portion of the septum) and the tip portion of the boot (at a central portion of the septum). The first mating means and second mating means are mated together, and while applying axial pressure to join the female luer connector component and spiked body, sonic energy is applied to weld the mating means and hence the members together. Under the influence of sonic energy, the mating means melt at their point of contact and move towards each other to form a strong fluid-tight fusion. As assembled in this fashion, the injection port is stabilized.

The septum is preferably provided with a pre-slit hole to facilitate the passage of the tip of the spike therethrough upon compression of the septum into the spike. The septum is also preferably designed to provide a small void between the septum and the tip portion of the boot such that the void space is available for the septum material to flow into during compression, as described below. Moreover, the surface of the septum at the second side is swabbable and is preferably provided with an external protuberance for centering a male luer thereon.

The length of the female luer connector component and/or the length of the spike is chosen so that when a male luer is inserted into the female luer, the male luer places pressure upon the septum which thereby urges the septum toward the spike. The pressure on the septum causes the spring portion of the boot to be compressed and the tip of the boot to be pierced by the tip of the spike. As the septum is further compressed, the septum extends over the spike, with the pre-slit hole facilitating the extension thereover, such that the spike is in fluid communication with the male luer connector. Fluid is then free to pass through the throughbore extending from the spike through the spiked body and to the male luer connector at the first end thereof. When the male luer is withdrawn from the female luer, the compressed spring-like portion of the boot expands and forces the tip of the boot back over the tip of the spike and the septum is withdrawn from the over the spike. The second end of the septum seats in the tapered opening of the female luer connector and is sealed, closing the port. It will be appreciated that the septum and the boot provide a double antibacterial barrier over the spike and significantly reduces incidence of pathogenic contamination of the injection port.

Minimal space is provided between the tip of the spike and the tip of the boot. As such, dead space is sufficiently reduced to minimize reflux. However, sufficient space is provided to facilitate recovery of the tip of the boot about the tip of the spike upon decompression of the boot after removal of a male luer connector from the female luer connector.

According to another aspect of the invention, a delivery system utlizing the injection port is also provided. The delivery system facilitates handling of the sterile injection port and coupling the injection port to an IV line.

Additional objects and advantages of the invention will become apparent to those skilled in the art upon reference to the detailed description in conjunction with the accompanying drawings.

DETAILED DESCRIPTION OF THE PREFERRED EMBODIMENTS

Figure 5:
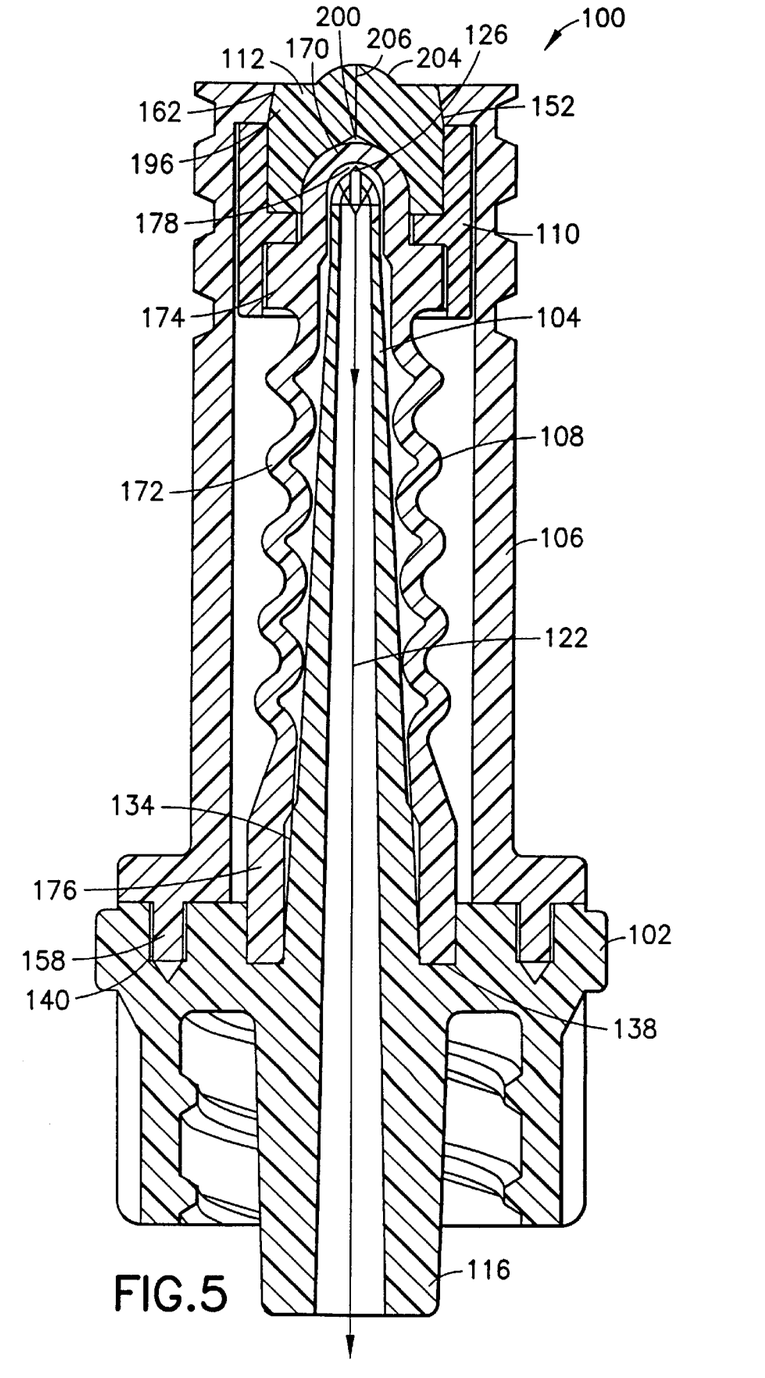
FIG. 5 is a section view of an injection port assembly according to a first embodiment of the invention shown in a closed position.

Turning now to FIG. 5, according to a first embodiment of a needleless IV injection port assembly 100 according to the invention generally includes a spiked body 102 provided with a hollow spike 104, a female luer connector component 106 (preferably a luer lock), a flexible and resilient spike boot 108, a washer-like centering member 110, and a resilient septum 112. As described in more detail below, the spike boot 108 extends over the spike 104, the centering member 110 is provided over a portion of the spike 104 and spike boot 108, and the septum 112 is provided between the centering member 110 and an end of the female luer connector component 106. The spiked body 102 and the female luer connector component 106 are then secured together to complete the assembly 100. The spiked body 102, the luer connector component 106, and the centering member 110 are preferably made from a hard plastic material, such as BASF Terlux™. The spike boot 108 and the septum 112 are preferably made from a rubber-like material, such as polyisoprene or silicone, having an approximately 30 Shore A Durometer.

Figure 6:
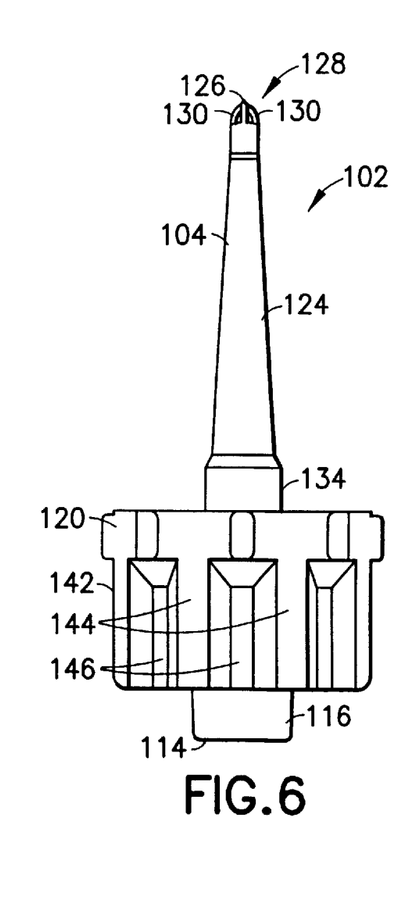
FIG. 6 is a side elevation view of a spiked body component of the injection port assembly shown in FIG. 5.
Figure 7:
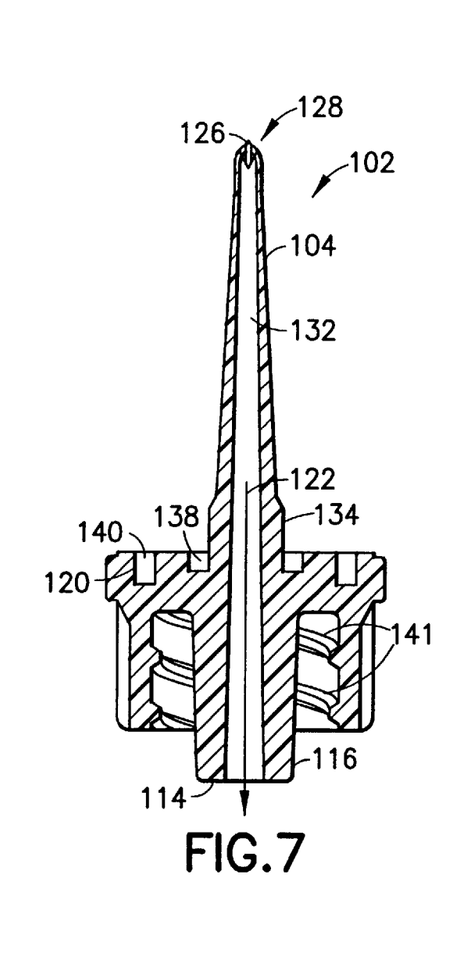
FIG. 7 is a section view of the spiked body component shown in FIG. 6.
Figure 8:
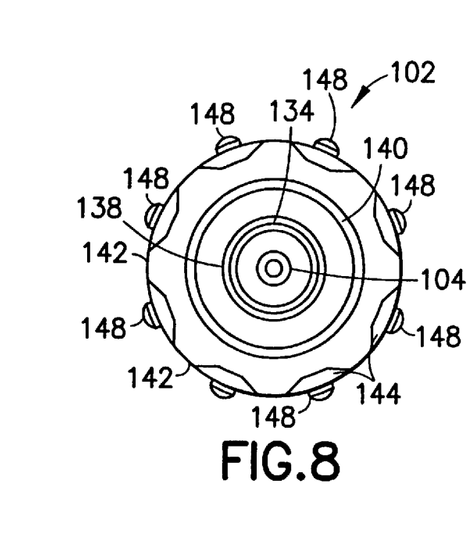
FIG. 8 is top view of the spiked body component shown in FIG. 6.

More particularly, referring to FIGS. 6 through 8, the spiked body 102 includes a first end 114 having a male luer connector 116, the spike 104, preferably integrally formed with the body 102 and coaxially directed opposite the male luer connector 116, and a base 120 at the juncture of the male luer connector 116 and the spike 104. A fluid path 122 is provided through the spike 104 and male luer connector 116. The spike 118 has a tapered shaft 124 leading to a sharp arched tip 126 which defines a second end 128 of the spiked body 102. The tip 126 includes a plurality of slots (e.g., four slots) 130 which provide access into the hollow 132 of the spike 104 from outside the spike. The shaft 124 includes a base portion 134 which has an enlarged stepped diameter for holding the boot 108 thereabout, as described below. The base 120 of the spiked body 102 also includes an annular groove 138 which further receives the boot, and a preferably annular mating slot 140. The base 120 preferably also includes a plurality of internal threads 141 which together with the male luer connector 116 function as a male luer lock. In addition, the periphery 142 of the base 120 includes a plurality of molded longitudinal ridges 144 and grooves 146 to facilitate engagement of the periphery 142 of the spiked body by human fingers. Furthermore, the base 120 includes a plurality of peripheral nubs 148 which engage with a housing of a delivery system, described below.

Figures 9, 10:
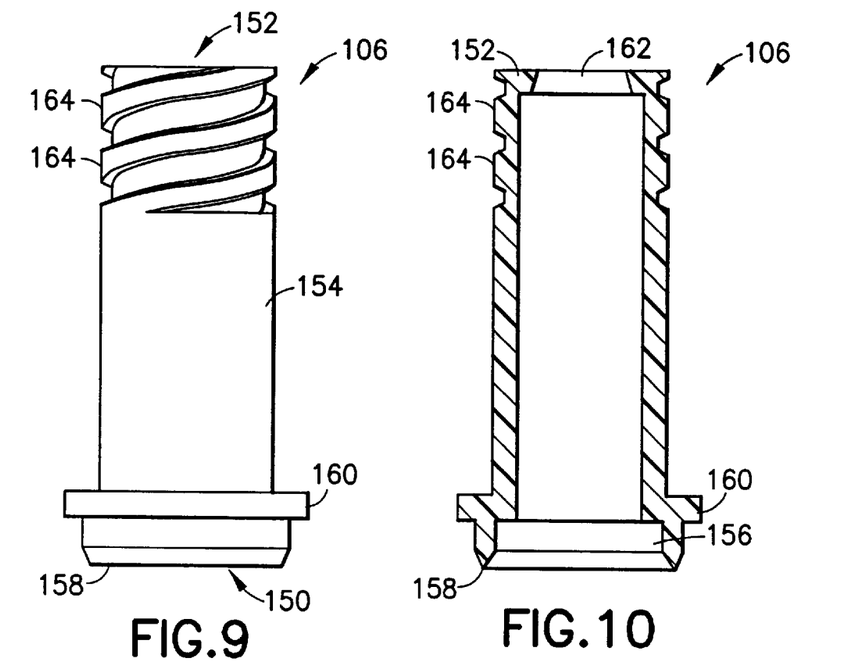
FIG. 9 is side elevation view of a female luer connector component of the injection port assembly shown in FIG. 5.
FIG. 10 is a section view of the female luer connector component shown in FIG. 9.

Turning now to FIGS. 5, 9 and 10, the female luer connector component 106 is tubular and includes a first open end 150, a female luer second end 152, and a central portion 154 therebetween. The first end 150 includes a lip 160 which is preferably provided with an annular mating ridge 158. The ridge defines an enlarged diameter relative to the central portion 154, and is provided on the lip 160 directed away from the second end 152. The mating ridge 158 is sized and shaped to be received in the annular mating slot 140 of the spiked body 102. The second end 152 includes an opening 162 having a reduced (relative to the rest of the component 106) and tapered diameter. A plurality of luer lock threads 164 are preferably provided about the second end 152.

Figures 11, 12, 13:
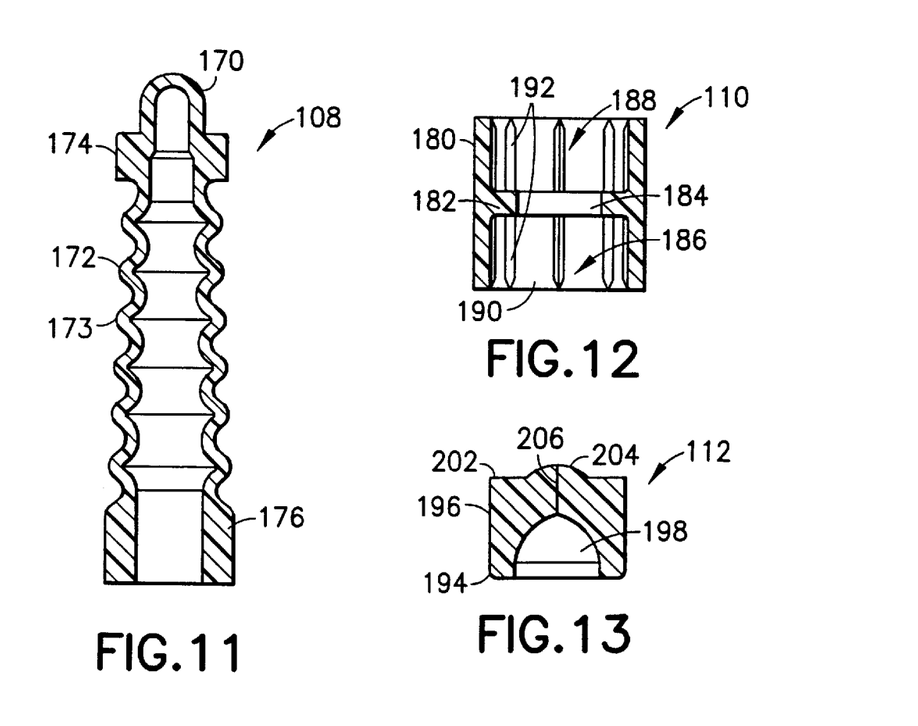
FIG. 11 is a section view of a spike boot component of the injection port assembly shown in FIG. 5.
FIG. 12 is a section view of a centering member of the injection port assembly shown in FIG. 5.
FIG. 13 is a section view of a septum component of the injection port assembly shown in FIG. 5.

Referring now to FIGS. 5 and 11, the spike boot 108 extends over the spike 104, and generally has a tip portion 170 which is sized to cover the tip 126 of the spike, a spring-like portion 172 sized to extend along the shaft of the spike and defining a plurality of undulations 173, a radially enlarged portion 174 between the tip portion 170 and the spring-like portion 172 and a base portion 176 sized to seat in the annular groove 138 about the base portion 134 of the spike 118. Between the tip portion 170 and the radially enlarged portion 174, the boot 108 is sized to substantially contact the spike 104. The tip portion 170 is sized to provide a very small cavity 178 (e.g., less than approximately 0.003 mL) between the tip 126 of the spike 104 and the tip portion of the boot 108.

Turning now to FIG. 12, the centering member 110 includes a generally tubular outer portion 180 and an annular central portion 182 provided with a hole 184. The outer portion 180 is sized to stably axially slide within the central portion 154 of the female luer component 106. The outer portion 180 and central portion 182 together define first and second receiving areas 186, 188. The tubular portion 180 includes an inner surface 190 provided with a plurality of engagement ridges 192 which engage the radially enlarged portion 174 of the spike boot 108 in the first receiving area 186 and which engage the septum 112 in the second receiving area 188.

Referring now to FIGS. 5 and 13, the septum 112 includes a first end 194 and a second end 196. The first end 194 has a diameter sized to be engaged by the engagement ridges 192 in the second receiving area 188 of the centering member 110 and is provided with a cavity 198 which receives the tip 170 of the spike boot 108. The cavity 198 is preferably sized and shaped to provide a small void 200 between the septum and the boot such that the void space is available for the septum material to flow into during compression (FIG. 5). The second end 196 includes a slightly tapered diameter portion 202 which is seatable within the tapered opening 162 of the second end 152 of the female luer connector component 106. In addition, an external protuberance 204 for centering a male luer connector is preferably provided at the second end 196. The second end 196 of the septum is swabbable. The septum 112 is also preferably provided with a pre-punctured slit (hole) 206 to facilitate movement of the tip 126 of the spike 104 through the septum 112 upon compression of the septum towards the spike.

Referring particularly to FIG. 5, in assembly, the spike boot 108 is positioned over the spike 104 with the base 176 of the boot seating over the base 134 of the spike and in the annular groove 138 in the base 120 of the spiked body 102. The centering member 110 is then positioned over the tip portion 170 of the boot such that on the radially enlarged portion 174 of the boot is provided in the first receiving area 186. The septum 112 is provided in the second receiving area 188 of the centering member 110, with the tip portion 170 of the boot 108 and the tip 126 of the spike 104 extending into the cavity 198. The female luer component 106 is extended over the septum 112, centering member 110, spike 104 and spike boot 108, with the tapered portion 202 of the septum 112 seated within the tapered opening 162 of the second end 152 of the female luer connector component 106. The mating ridge 158 of the female luer connector component 106 is mated with the annular mating groove 140 in the spiked body 102, and while applying axial pressure to join the female luer connector and spiked body, sonic energy is applied to weld the mating means and hence the members together. Under the influence of sonic energy, the ridge and groove mating means melt at their point of contact and move towards each other to form a strong fluid-tight fusion. As assembled in this fashion, the injection port is stabilized, with the centering member 110 and septum 112 biased by the spring-like portion 172 of the spike boot 108 towards the second end 152 of the female luer connector 106. It will be appreciated that the spike boot 108 and septum 112 provide a swabbable antibacterial double barrier over the spike 104.

Figure 14:
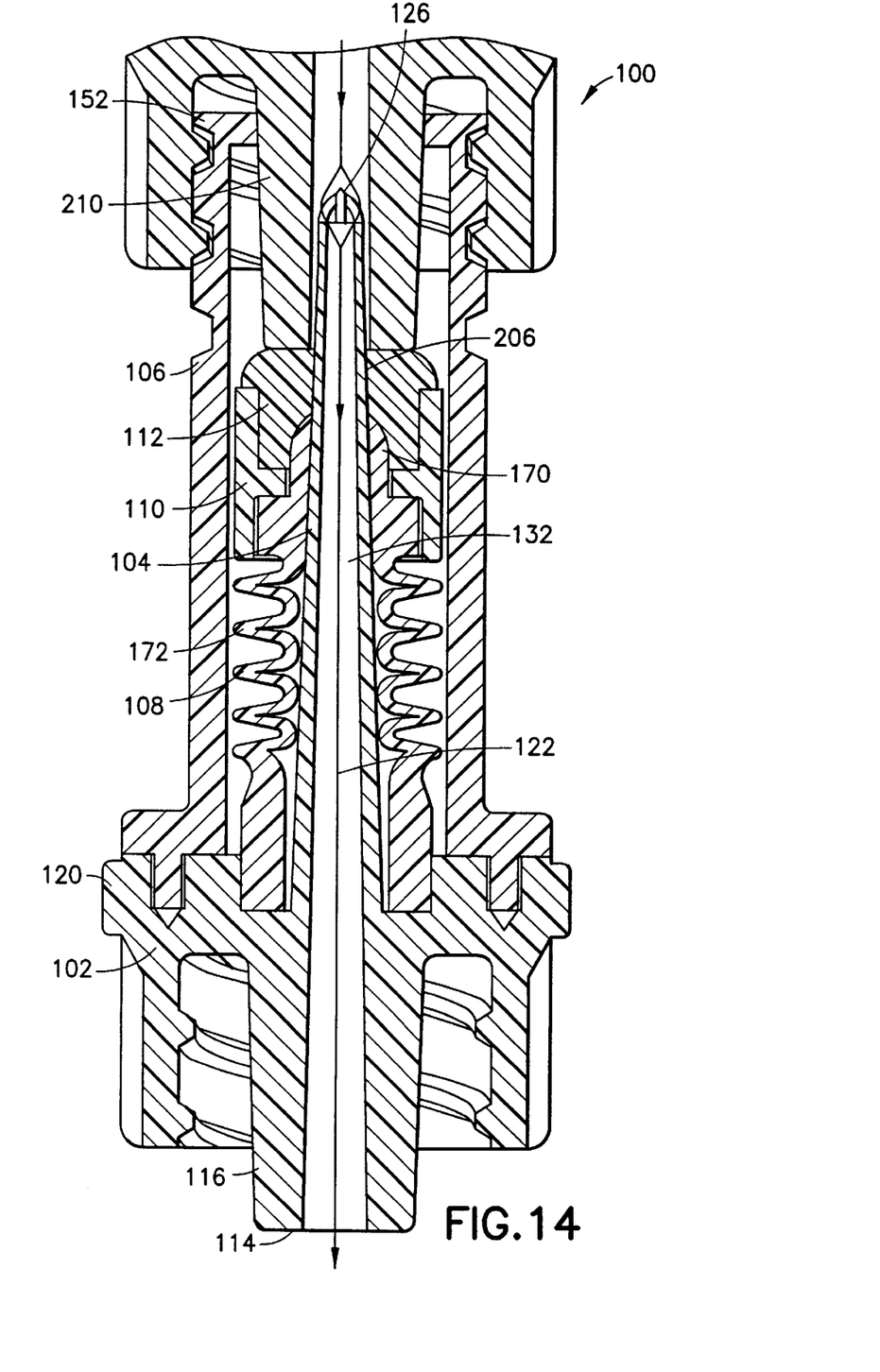
FIG. 14 is a section view of the injection port assembly according to the first embodiment of the invention shown in an open position.

Referring to FIGS. 5 and 14, the length of the female luer connector component 106 and/or the length of the spike 104 is chosen so that when a separate male luer 210 (preferably provided with a luer lock) from another device (such as a syringe) is centered over the protuberance 204 on the septum 112 and pushed into the female luer connector component 106 (preferably by rotation such that the male and female luer locks threadably engage), the separate male luer 210 places pressure upon the septum 112 which thereby urges the septum toward the tip 126 of the spike 104. The pressure on the septum 112 causes the spring-like portion 172 of the boot 108 to be compressed and the tip portion 170 of the boot to be pierced by the tip 126 of the spike 104. As the septum 112 is further compressed, the septum extends over the spike 104, with the pre-slit hole 206 facilitating the extension thereover, such that the hollow 132 of the spike is in fluid communication with the separate male luer connector 210. Fluid is then free to pass through the fluid pathway 122 extending from the spike 104 through the base 120 of spiked body 102 and to the male luer connector 116 at the first end 114 thereof. When the separate male luer connector 210 is withdrawn from the second end 152 of the female luer connector component 106, the resilient boot spring 172 expands and forces the tip portion 170 of the boot back over the tip 126 of the spike and the septum 112 is pushed over the tip of the spike, thereby providing a first seal. The tapered second end 196 of the septum 112 reseats in the tapered opening 162 of the second end 152 of the female luer connector 106, thereby providing a second seal for the injection port 100. The centering member 110 functions as a stop against the constricted opening 152 of the female connector 106. The combination of the first and second seals provides an enhanced antimicrobial barrier to the injection port assembly. It will be appreciated that the double barrier operates as a pathogenic barrier into the injection port and also as a pathogenic barrier from the injection port; i.e, to prevent leakage of the patient's blood from the injection port.

Furthermore, it will be appreciated that the approximately 0.003 mL (or smaller) cavity 178 between the tip portion 170 of the boot 108 and the tip 126 of the spike 104 is sufficiently small to substantially eliminate reflux after the removal of the separate male luer component. As such, the design of the invention substantially eliminates the potential negative effects of reflux on the IV system. Nevertheless, the provided cavity is of sufficient space to facilitate recovery of the tip portion 170 of the boot about the tip 126 of the spike upon decompression of the boot after removal of the male luer connector 210 from the female luer connector. In addition, the priming volume of the injection port assembly is relatively small, approximately only 0.03 mL, and the fluid flow through the port is excellent, at upwards of 185 mL per minute.

Figure 15:
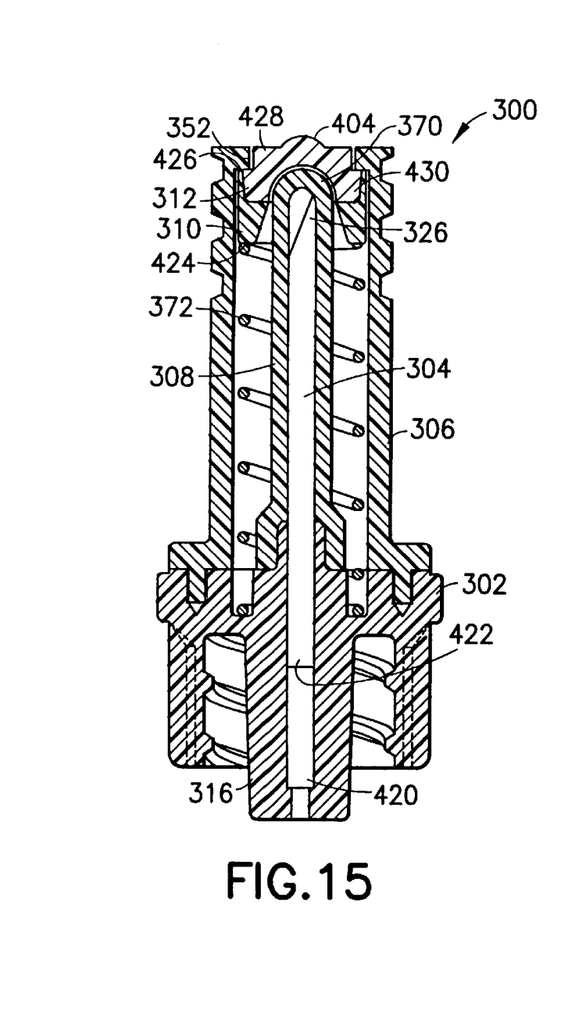
FIG. 15 is a transparent partial section view of an injection port assembly according to a second embodiment of the invention shown in a closed position.

Turning now to FIG. 15, a second embodiment of a needleless IV injection port assembly 300 according to the invention, substantially similar to the first embodiment (with like parts having numbers incremented by 200) is shown. The injection port assembly 300 includes a body 302 preferably provided with a male luer connector 316 and an axial throughbore 420, a hollow spike 304 (e.g., stainless steel needle) provided with a first end 422 which is coupled in the axial throughbore 420 and a penetrating tip 326 at an opposite end, and a female luer connector component 306 (preferably a luer lock) extending over the spike 304 and coupled to the body 302. A flexible, resilient, and preferably substantially tubular boot 308 extends over the spike 304, and a washer-like centering member 310 resides over the tip 370 of the boot 308. The centering member 310 includes a lower spring seat 424 and an upper annular stop 426. A coil spring member 372 (either made from plastic or metal) extends around the boot 308 between the body 302 and the spring seat 424 of the centering member 310. A resilient septum 312 is provided between the centering member 310 and the open end 362 of the female luer connector component 306 and includes an external protuberance 404, and a stepped diameter. The stepped diameter includes a first diametered portion 428 sized to seat within the constricted opening 352 of the female luer connector component 306, and a second diametered portion 430 sized large enough to abut the interior of the female luer connector component surrounding the constricted opening 352. Alternatively, the septum and open end of female luer connector component may be of the configurations described above with respect to the first embodiment of the invention. The septum 312 forms an outer first antimicrobial seal, and the boot 308 forms an inner second antimicrobial seal preferably in contact with the septum 312.

Figure 16:
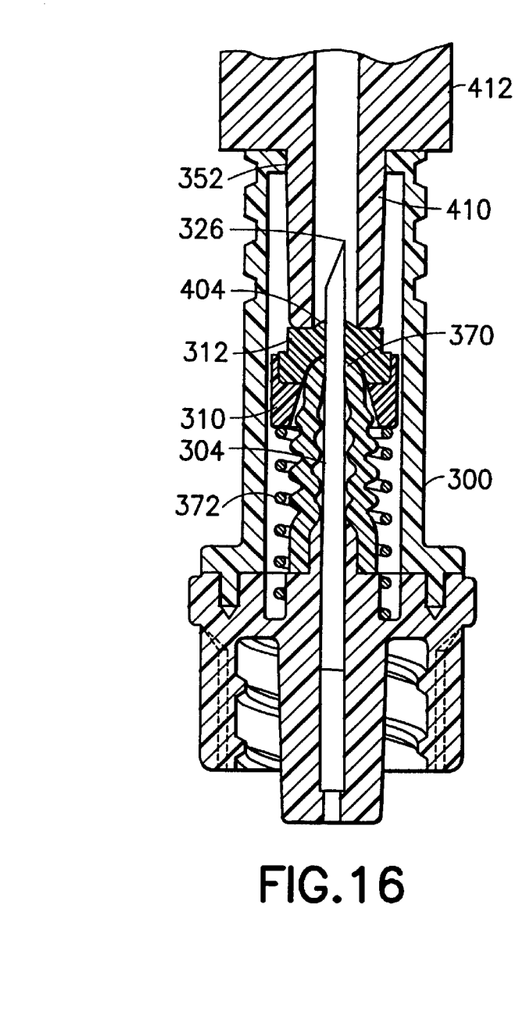
FIG. 16 is a section view of the injection port assembly according to the second embodiment of the invention shown in an open position.

Referring now to FIG. 16, in use, a separate male luer 410 (preferably provided with a luer lock) from another device 412 (such as a syringe) is centered over the protuberance 404 on the septum 312 and pushed into the female luer connector component 306. The separate male luer 410 places pressure upon the septum 312, and urges the septum toward the tip 326 of the spike 304, while the centering member 310 is moved to compress the spring 372. Further movement causes the tip portion 370 of the boot to be pierced by the tip 326 of the spike 304 and the septum 312 to also be pierced by the tip 326 such that the hollow spike 304 is in fluid communication with the separate male luer connector 410. Fluid is then free to pass between the male luer connector 410 and the injection port 300. When the separate male luer connector 410 is withdrawn from the open end 352 of the female luer connector component 306, the coil spring 372 automatically expands and forces the centering member 310 back toward the constricted open end 352 of the female luer component 306. The septum 312 is thereby pushed over the tip 326 of the spike 304 and reseals the injection port 300. As the septum 312 returns to its stationary position, the boot 308 resiliently expands to likewise cover and reseal over the tip 326 of the spike 304.

Figure 17:
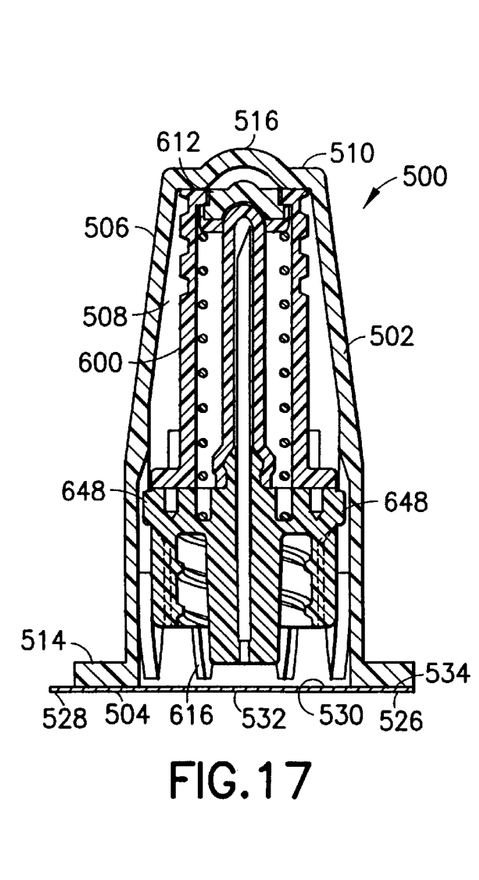
FIG. 17 is a section view of an injection port delivery system according to the invention, provided with an injection port therein.
Figure 18:
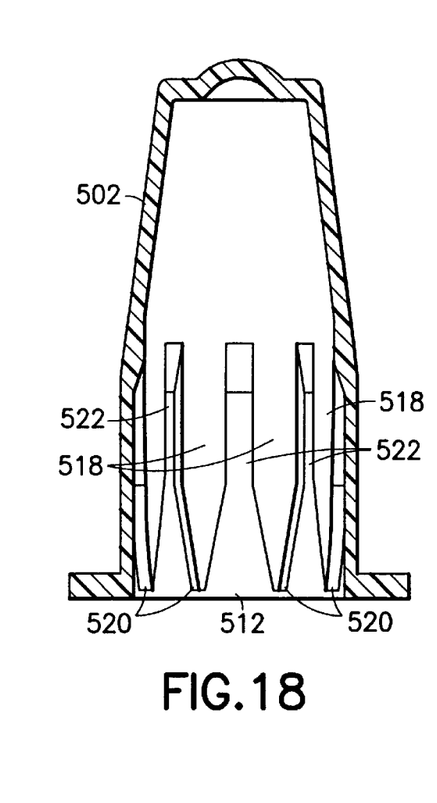
FIG. 18 is a section view of a housing portion of the packaging assembly.
Figure 19:
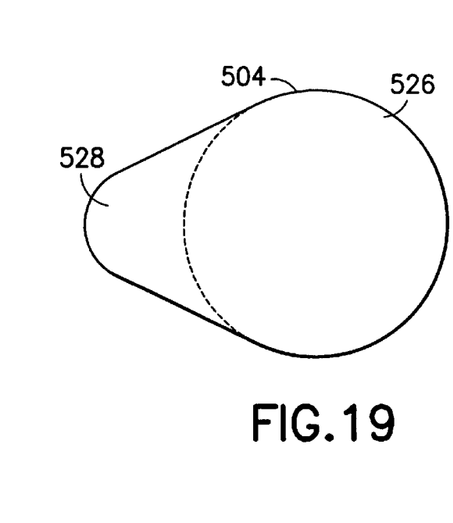
FIG. 19 is a bottom view of the packaging assembly illustrating a preferred shape for the lid of the packaging assembly.

Turning now to FIGS. 17 through 19, according to a preferred aspect of the invention, the injection port according the various embodiments of the invention is provided as part of a delivery system 500. The delivery system 500 includes a housing 502, an injection port 600 provided in the housing 502, and a lid 504 sealing the injection port 600 in the housing 502. The housing 502 is preferably comprised of a substantially rigid, preferably clear plastic and includes an exterior surface 506, a generally tubular interior surface 508, a closed first end 510, and an open second end 512 provided with a peripheral flange 514. The closed first end 510 is optionally provided with a central dome 516. At least a portion of the interior 508 is molded (or otherwise provided) with a plurality of a ridges 518, each preferably tapering to a blunt point 520 at the second end 512, defining slots 522 therebetween.

The injection port 600 is preferably substantially as described above in the first and second embodiment (with like parts having numbers incremented by 500 relative to the first embodiment). After the interior of the housing 502 has been sterilized, a sterilized injection port 600 is easily positioned in the housing 502, with the septum 612 provided adjacent, yet not in contact with, the dome 516 of the housing. The nubs 648 on the body 606 of the injection port 600 are guided by the blunt points 520 to enter into the slots 522 in the housing 502. As such, the housing 502 and injection port 600 may not be rotated relative to each other once the injection port is properly seated in the housing. In addition, when properly seated, the male luer connector 616 on the injection port 600 resides within the housing and no additional shield is required over the connector 616, as required by prior art injection port devices.

The lid 504 is preferably manufactured from a foil or thin sheet material such as Tyvek™, available from Dupont. The lid 504 is preferably teardrop shaped and has a circular portion 526 and a tab portion 528. The lid 504 includes an inside 530 which faces the flange 514, and an exterior side 532. The inside 530 is provided with an adhesive 534, at least around the periphery of the circular portion 526, which couples the lid 504 to the flange 514 such that the circular portion 526 seals the open second end 512 of the housing 502. The lid 504 provides a flat support on which the delivery system 500 may be stood upright. The tab portion 528 extends from the periphery of the flange 514, and provides a means for opening the delivery system for access to the injection port 600.

It will be appreciated that the delivery system 500 provides function in addition to providing a compact sterilized package for the shipping and storage of an injection port 600. The delivery system 500 further assists in manipulating the injection portion 600 without directly handling the injection port 600. That is, the lid 504 may be manually gripped by a health care worker at the tab portion 528 and peeled off the second end 512 of the housing 502, thereby exposing male luer connector 616 on the body 602 of the injector port 600. The health care worker may then hold and manipulate the exterior surface 506 of the housing 502 to couple the male luer connector 616 to another device, e.g., an IV line luer lock connector. It will be appreciated that because the housing 502 and injection port 600 are rotatably locked together at the nubs 648 and ridges 518, respectively, rotation of the housing 502 by the health care worker operates to thread the luer connector 616 to the other device. Once the injection port 600 is coupled to the other device, the housing 502 may then be axially withdrawn from over the injection port 600 to expose the septum 612, which has previously been maintained within the sterile interior 508 of the housing 502. The injection port 600 then may be utilized as previously described.

There have been described and illustrated herein several embodiments of medical IV administration injection port. While a particular embodiment of the invention has been described, it is not intended that the invention be limited thereto, as it is intended that the invention be as broad in scope as the art will allow. Thus, it will be appreciated by those skilled in the art that the term "IV fluid" is intended to be understood in a broad sense to include parenteral fluids including drug solutions, blood, blood products, dyes, or other fluids and the term "administration" is used in its broad sense to include the dispensing or collection of the "IV fluid". Further, while the injection port is illustrated as preferably having a female luer lock on one end, and a male luer lock on the other end, it will be appreciated that, although not preferred, simple luer slips could be utilized in lieu of luer locks. It will also be understood that while one end of the connector should, though not necessarily must, be a female coupling, it is not necessary that the other end of the connector be a male coupling. Moreover, while it is presently preferred to include a small cavity between the tip of the spike and the tip portion of the boot, it will be appreciated that no cavity therebetween is required, only that such a cavity facilitates spike boot recovery. Any such cavity should minimize reflux by being as small as possible while still assisting in boot recovery. Furthermore, while a ridge and groove are disclosed for mating the female luer component and spiked body together, it will be appreciated that other mating means may be used. For example, a plurality of mating tabs and slots, or ridges and grooves, or the like, may be used. In addition, while the septum and tip portion are disclosed as preferably forming a small void therebetween to facilitate movement of the septum over the spike, it will be appreciated that no such void is required. Moreover, while a particular plastic material has been disclosed for the spiked body, female luer component, and centering member, it will be appreciated that other rigid materials may likewise be used for these components. Also, in each embodiment the spike may be unitary with or of a separate construction than the body. Furthermore, while particular rubber-like materials have been disclosed for the spike boot and septum, it will be appreciated that other rubber-like materials of different Durometers may also be used. In addition, while particular tip configurations of the spike have been shown and described, it will be appreciated that the tip may otherwise be formed. For example, the tip may comprise one or more arches and be provided with various penetrating angles at the tip. Moreover, while the packaging assembly has been described for use with an injection port according to the invention, it will be appreciated that the packaging assembly may alternatively be provided with injection ports existing in the art and future developed injection ports. Therefore, it will be appreciated by those skilled in the art that yet other modifications could be made to the provided invention without deviating from its spirit and scope as so claimed.

What is claimed is:

1. An injection port delivery system for an injection port adapted to couple to a first fluid pathway of a first connector and for receiving and passing a fluid into the first fluid pathway from a device provided with a second connector, said delivery system comprising:
    a) a substantially rigid housing having an interior, an exterior surface, a closed first end, and an open second end;
    b) an injection port including a first coupling means for coupling to the first connector, a second coupling means for coupling to the second connector, a hollow spike, a resilient barrier between said hollow spike and said second connector, said injection port provided in said interior of said housing with said first coupling means provided adjacent said second end of said housing; and
    c) a lid sealing said second end of said housing to enclose said injection port within said housing.

2. A delivery system according to claim 1, wherein:
said housing is comprised of a clear plastic.

3. A delivery system according to claim 1, wherein:
said first closed end of said housing is provided with a dome.

4. A delivery system according to claim 1, wherein:
said lid defines a circular portion and a tab portion.

5. A delivery system according to claim 1, wherein:
a space is defined between said resilient barrier and said closed first end of said housing.

6. A delivery system according to claim 1, wherein:
said resilient barrier and said closed first end of said housing are not in contact.

7. A delivery system according to claim 1, wherein:
said resilient barrier comprises first and second resilient barriers.

8. A delivery system according to claim 1, wherein:
said second open end of said housing is provided with a peripheral flange to which said lid is coupled.

9. A delivery system according to claim 8, wherein:
said lid is coupled to said flange with an adhesive.

10. A delivery system according to claim 1, wherein:
said housing includes first locking means and said injection port means includes second locking means, said first and second locking means for rotatably interlocking said housing relative to said injection port means.

11. A delivery system according to claim 10, wherein:
said first locking means is at least one slot provided along said interior of said housing and said second locking means is at least one raised portion on said injection port means which is positionable within said at least one slot.

12. A delivery system according to claim 11, wherein:
said at least one slot is a plurality of slots and said plurality of slots are defined by a plurality of ridges along said interior of said housing.

13. A delivery system according to claim 12, wherein:
each of said plurality of ridges has a substantially pointed end.

* * * * *